United States Patent [19]

Tsuboi et al.

[11] Patent Number: 5,457,052
[45] Date of Patent: Oct. 10, 1995

[54] PROCESS FOR THE PREPARATION OF OPTICALLY ACTIVE 3-CHLORO-1-PHENYL-PROPANOL BY A LIPASE CATALYZED HYDROLYSIS

[75] Inventors: Sadao Tsuboi, Okayama; Masayuki Negoro, Hyogo; Masanori Udaka, Okayama; Michio Ito; Yoshinori Kobayashi, both of Niigata, all of Japan

[73] Assignee: Daicel Chemical Industries, Ltd., Osaka, Japan

[21] Appl. No.: 232,589

[22] Filed: Apr. 25, 1994

Related U.S. Application Data

[63] Continuation of Ser. No. 930,680, filed as PCT/JP92/00159, Feb. 18, 1992, abandoned.

[30] Foreign Application Priority Data

Feb. 19, 1991 [JP] Japan .................................. 3-024529

[51] Int. Cl.$^6$ ....................................................... C12P 41/00
[52] U.S. Cl. ........................ 435/280; 435/822; 435/917; 435/921; 435/933; 435/939
[58] Field of Search ............................... 435/280, 822, 435/917, 921, 933, 939

[56] References Cited

U.S. PATENT DOCUMENTS

| | | | |
|---|---|---|---|
| 4,868,344 | 9/1989 | Brown | 568/812 |
| 4,963,492 | 10/1990 | Keller et al. | 435/280 |

FOREIGN PATENT DOCUMENTS

| | | |
|---|---|---|
| 0288994 | 11/1988 | European Pat. Off. . |
| 321918 | 6/1989 | European Pat. Off. . |
| 2241953 | 9/1991 | United Kingdom . |

OTHER PUBLICATIONS

Okumara et al, Biochim et Biophys Acta 575:156–65 (1979).
Hills et al, Biochim et Biophys Acta 1042:237–40 (1990).
Fuelliner et al, Oppor. Biotransform [PAP Conf] 186–94 (1990).
Baratti et al, Proc. World Conf Emerging Technol. Fats Oils Ind. Am Oil Chem Soc 355–8 (1985).
Langrand et al, Tetrahedron Letts 27:29–32 (1986).
K. Laumen et al. J. Chem. Soc., Chem. Commun., (1988) pp. 598–600.

*Primary Examiner*—Marian C. Knode
*Assistant Examiner*—S. Saucier
*Attorney, Agent, or Firm*—Birch Stewart Kolasch & Birch

[57] ABSTRACT

An enantiomeric mixture of a 3-chloro-1-(substituted) phenyl-1-propyl ester of a saturated or unsaturated aliphatic acid is treated with an enzyme which can asymmetrically hydrolyze the mixture, for example, a lipase originating in a microorganism of the genus Pseudomonas, Aspergillus, Candida or Chromobacterium to form a mixture of an optically active 3-chloro-1-(substituted) phenyl-1-propanol with an optically active 3-chloro-1-(substituted) phenyl-1-propyl ester of a saturated or unsaturated aliphatic acid, and the optically active 3-chloro-1-(substituted) phenyl-1-propanol or a derivative thereof and the optically active 3-chloro-1-(substituted) phenyl-1-propyl ester of a saturated or unsaturated aliphatic acid or a derivative thereof are each separately recovered from the mixture. The process allows simple and easy preparation of the above optically active compounds having a high optical purity, thus being extremely industrially advantageous.

10 Claims, No Drawings

PROCESS FOR THE PREPARATION OF OPTICALLY ACTIVE 3-CHLORO-1-PHENYL-PROPANOL BY A LIPASE CATALYZED HYDROLYSIS

This application is a continuation of application Ser. No. 07/930,680 filed on Oct. 13, 1992, now abandoned.

BACKGROUND OF THE INVENTION

1. Field of the Invention

The present invention relates to a process for the preparation of an optically active 3-chloro-1-(substituted) phenyl-1-propanol and an optically active 3-chloro-1-(substituted-)phenyl-1-propyl ester of a saturated or unsaturated aliphatic acid, and derivatives thereof.

These optically active compounds are important as the intermediates for the synthesis of drugs.

2. Description of Background Art

Up to this time, chemical asymmetric reduction of 3-chloropropiophenone (see U.S. Pat. No. 486834 and Tetrahedron Lett., 30, 5207 (1989)) and transesterification thereof with lipase (see Japanese Patent Publication-A No. 202296/1989) have been known as the processes for the preparation of optically active 3-chloro-1-phenyl-1-propanol. However, the chemical asymmetric reduction is disadvantageous as an industrial process, because the asymmetric reducing agent is expensive. On the other hand, the transesterification with lipase is disadvantageous in that the obtained product has only a poor optical purity.

Under these circumstances, the establishment of a process for preparing optically active 3-chloro-1-phenyl-1-propanol or derivative thereof, and an optically active 3-chloro-1-phenyl-1-propyl ester of an aliphatic acid or a derivative thereof, each of which has a high optical purity, by an economical and simple means has been expected.

SUMMARY OF THE INVENTION

It is an object of the present invention to obtained an enzymatic process using an enantiomeric mixture of a 3-chloro-1-phenyl-1-propyl ester of an aliphatic acid as a starting material for preparing optically active 3-chloro-1-phenyl-1-propanol and an optically active 3-chloro-1-phenyl-1-propyl ester of an aliphatic acid, each of which has a high optical purity, which is economical and simple. It is a further object of the present invention to provide an enzyme suitable for this purpose. More particularly, it is an object of the present invention to provide an enzyme which can asymmetrically hydrolyze the starting mixture to accomplish the present invention.

These and other object of, the present invention are achieved by providing a process for the preparation of optically active 3-chloro-1-phenyl-1-propanol and derivatives thereof, comprising a step of treating an enantiomeric mixture of a 3-chloro-1-(substituted) phenyl-1-propyl ester of a saturated or unsaturated aliphatic acid, represented by the following general formula (1), with an enzyme which asymmetrically hydrolyzes the enantiomeric mixture to form a mixture comprising an optically active 3-chloro-1-(substituted) phenyl-1-propanol and an optically active 3-chloro-1-(substituted) phenyl-1-propyl ester of a saturated or unsaturated aliphatic acid:

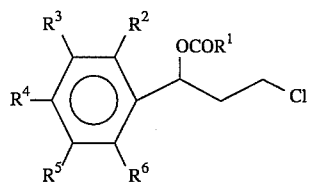

wherein $R^1$ is a saturated or unsaturated, straight chain or branched monovalent hydrocarbon group having 1 to 18 carbon atoms or a saturated or unsaturated, straight-chain or branched monovalent halogeno-hydrocarbon group having 1 to 18 carbon atoms; and $R^2$, $R^3$, $R^4$, $R^5$ and $R^6$ are independent from each other each a hydrogen atom, a halogen atom, a nitro group, a hydroxyl group, a straight-chain or branched alkyl group having 1 to 6 carbon atoms or an alkoxy group, the alkyl moiety of which is straight-chain or branched and has 1 to 4 carbon atoms.

A preferred embodiment of the claimed process comprises preparing a mixture of an optically active 3-chloro-1-(substituted) phenyl-1-propanol with an optically active 3-chloro-1-(substituted) phenyl-1-propyl ester of a saturated or unsaturated aliphatic acid through the above-mentioned step and thereafter separately recovering the optically active 3-chloro-1-(substituted) phenyl-1-propanol and the optically active 3-chloro-1-(substituted) phenyl-1-propyl ester of a saturated or unsaturated aliphatic acid from the mixture.

Another preferred embodiment of the claimed process comprises preparing a mixture of an optically active 3-chloro-1-(substituted) phenyl-1-propanol with an optically active 3-chloro-1-(substituted) phenyl-1-propyl ester of a saturated or unsaturated aliphatic acid through the above-mentioned step, chemically treating the mixture to convert at least either of the optically active 3-chloro-1-(substituted) phenyl-1-propanol and the optically active 3-chloro-1-(substituted) phenyl-1-propyl ester of a saturated or unsaturated aliphatic acid into a derivative, and separately recovering the optically active 3-choro-1-(substituted) phenyl-1-propanol or a derivative thereof and the optically active 3-chloro-1-(substituted) phenyl-1-propyl ester of a saturated or unsaturated aliphatic acid or a derivative thereof from the resulting mixture.

DETAILED DESCRIPTION OF THE INVENTION

The raw material to be used in the present invention is an enantiomeric mixture of a 3-chloro-1-(substituted) phenyl-1-propyl ester of a saturated or unsaturated aliphatic acid represented by the above general formula (1).

In the above general formula (1), $R^1$ is a saturated or unsaturated, straight-chain or branched monovalent hydrocarbon group having 1 to 18 carbon atoms or a saturated or unsaturated, straight-chain or branched monovalent halogenohydrocarbon group having 1 to 18 carbon atoms. That is, $R^1$ is a group selected from among straight-chain and branched alkyl, alkenyl, alkynyl, halogenoalkenyl, halogenalkenyl and halogeno-alkynyl groups having 1 to 18 carbon atoms.

Specific examples of $R^1$ include a methyl group, an ethyl group, an n-propyl group, an isopropyl group, an isopropenyl group, an n-butyl group, an isobutyl group, a hexyl group, a heptadecyl group, a heptadecynyl group, an n-pentadecynyl group, a monochloromethyl group, a dichloromethyl group, a trichloromethyl group, a trichloroethyl group and a vinyl group.

Further, $R^2$, $R^3$, $R^4$, $R^5$ and $R^6$ are independent from each other and each maybe a hydrogen atom, a halogen atom, a nitro group, a hydroxyl group, a straight-chain or branched alkyl group having 1 to 6 carbon atoms or an alkoxy group, the alkyl moiety of which is straight-chain or branched and has 1 to 4 carbon atoms.

The phenyl moiety of the compound represented by the general formula (1) wherein at least one of $R^2$, $R^3$, $R^4$, $R^5$ and $R^6$ is a group of atoms other than a hydrogen atom is called "substituted phenyl group".

Specific examples of the halogen atom include chlorine atom and fluorine atom; examples of the straight-chain and branched alkyl groups having 1 to 6 carbon atoms include a methyl group, an ethyl group, a propyl group and so on; and examples of the alkoxy group, the alkyl moiety of which is straight-chain or branched and has 1 to 4 carbon atoms, include a methoxy group, an ethoxy group and so on. These substituents may be each present at any of the positions, that is, ortho, meta or para, with respect to the substituted propyl group (represented by the formula:

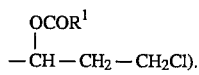

Examples of the compound represented by the above general formula (1) include those represented by the formula (1) wherein $R^1$ is an aliphatic hydrocarbon group having 1 to 8 carbon atoms; and $R^2$, $R^3$, $R^4$, $R^5$ and $R^6$ are each a hydrogen atom, 1-acetoxy-3-chloro-1-phenylpropane corresponding to a compound represented by the formula (1) wherein $R^1$ is a methyl group and $R^2$, $R^3$, $R^4$, $R^5$ and $R^6$ are each a hydrogen atom, 1-acetoxy-3-chloro-1-(4-nitrophenyl)propane corresponding to a compound represented by the formula (1) wherein $R^1$ is a methyl group, $R^4$ is a nitro group and $R^2$, $R^3$, $R^5$ and $R^6$ are each a hydrogen atom, and 1-acetoxy-3-chloro-1-(4-hydroxyphenyl)propane corresponding to a compound represented by the formula (1) wherein $R^1$ is a methyl group, $R^4$ is a hydroxyl group and $R^2$, $R^3$, $R^5$ and $R^6$ are each a hydrogen atom.

It is preferable from the standpoint of cost that the enantiomeric mixture of a 3-chloro-1-(substituted) phenyl-1-propyl ester of a saturated or unsaturated aliphatic acid to be used as the raw material, i.e., a substrate of an enzyme, in the present invention be a racemic modification. The optical isomer ratio of the enantiomeric mixture to be used in the present invention is not particularly limited, and suitable ratio may be used.

The enzyme to be used in the present invention is not particularly limited, but may be any enzyme that can asymmetrically hydrolyze the above-mentioned enantiomeric mixture.

Examples of such an enzyme include lipases which originate in microorganisms selected from among those of the genera Pseudomonas, Aspergillus, Candida, Chromobacterium, penicillium, Geotrichum and Rhizopus and can attain the object of the present invention. Further, a lipase originating in swine pancreas may be also cited.

Particularly, a lipase originating in a microorganism of the genus Pseudomonas or Aspergillus is preferable.

Among pseudomonas-originating lipases, one orginating in Pseudomonas sp, is preferable; among aspergillus-originating lipases, one originating in *Aspergillus niger* is particularly preferable; among candida-originating lipases, one originating in *Candida cylindracea* is preferable; and among chromobacterium-originating lipases, one originating in *Chromobacterium viscosum* is preferable.

Further, among penicillium-originating lipases, one originating in *Penicillium cyclopium* is preferable; among geotrichum-originating lipases, one originating in *Geotrichum candidum* is preferable; and among rhizopus-originating lipases, those originating in *Rhizopus japonicus* and *Rhizopus niveus* are preferable.

Such a lipase can be prepared by culturing a microorganism which can produce it. The lipase may be used in various forms, including untreated culture mixture, crude enzyme, purified enzyme and so forth and the form thereof is not particularly limited. Alternatively, the enzyme may be used immobilized on a support by various conventional processes. These enzymes may be used either alone or as a mixture of two or more of them as needed or desired.

Among the above lipases, a lipase originating in Pseudomonas sp. is commercially available as "Lipase P, Amano" (a product of Amano Seiyaku K.K.) or "Lipase PS, Amano" (a product of Amano Seiyaku K.K.); a lipase originating in *Aspergillus niger* is commercially available as "Lipase A-6, Amano" (a product of Amano Seiyaku K.K.), "Lipase A-12, Amano" (a product of Amano Seiyaku K.K.) or "Palatase A750L (a product of Novo); a lipase originating in *Candida cylindracea* is commercially available as "Lipase MY" (a product of Meito Sangyo Co., Ltd.) or "Lipase OF" (a product of Meito Sangyo Co., Ltd. ); a lipase originating in *Chromobacterium viscosum* is commercially available as "Lipase" (a product of Toyo Jozo Co., Ltd.); a lipase originating in *Penicillum* cyclopium is commercially available as "Lipase G, Amano" (a product of Amano Seiyaku K.K.); lipase originating in *Geotrichum candidum* is commercially available as "Lipase GC, Amano 20" (a product of Amano Seiyaku K.K,); one originating in Rhizopus japonicus as "Lipase F-AP, Amano 15" (a product of Amano Seiyaku K.K.); a lipase originating in *Rhizopus niveus* is commercially available as "Newlase F, Amano 3"; and a lipase originating in swine pancreas is commercially available as "Steapsin" (a product of Tokyo Kasei K.K.). The use of these commercially available lipases is preferable.

According to the present invention, the asymmetric hydrolysis is conducted in an aqueous solvent at a substrate (raw material) concentration ranging from 0.1 to 80% (w/v), preferably from 1 to 30% (W/v) at a temperature of 0 to 80° C, preferably 10 to 60° C., still more preferably 20 to 50° C., particularly preferably at a temperature near the optimum temperature of the enzyme with either stirring or allowing the mixture to stand, preferably with stirring, with the enzyme being used in an amount necessary for attaining the object, e.g., at a weight ratio of the enzyme to the substrate of between 1:0.1 and 1:1000, preferably between 1:1 and 1: 100, depending on the enzyme acitivity. It is preferable in some cases that the pH of the reaction system be controlled. The pH may be controlled either by using a suitable buffer as the aqueous solvent or by the use of an aqueous solution of sodium hydroxide, potassium hydroxide or the like and a pH-stat. The reaction is monitored by various analytical methods, such as gas chromatography or high-performance liquid chromatography, by which the amount of the product formed, the optical purity thereof, and so forth can be determined. The reaction may be stopped at a suitable point in time. The reaction may be stopped by the addition of a suitable organic solvent, acid or alkali to the reaction system.

By the asymmetric hydrolysis, only one optically active compound is hydrolyzed into an alcohol corresponding thereto, while the other remains as such, i.e., in the form of an ester. Which of the R-and S-enantiomers is hydrolyzed depends on the kind of the enzyme used, the strain of the microorganism producing the enzyme, and so forth.

The present invention relates to a process for the preparation of an optically active 3-chloro-1-(substituted) phenyl-1-propanol and a derivative thereof, comprising a step of treating an enantiomeric mixture of a 3-chloro-1-(substituted) phenyl-1-propyl ester of a saturated or unsaturated aliphatic acid represented by the above general formula (1) with an enzyme which can asymmetrically hydrolyze the enantiomeric mixture to form a mixture comprising an optically active 3-chloro-1-(substituted) phenyl-1-propanol and an optically active 3-chloro-1-(substituted) phenyl1-propyl ester of a saturated or unsaturated aliphatic acid, and is not particularly limited with respect to the treatment method (post step) of the obtained mixture comprising the optically active 3-chloro-1-(substituted) phenyl-1-propanol and the optically active 3-chloro-1-(substituted) phenyl-1-propyl ester of a saturated or unsaturated aliphatic acid.

One example of the post step is direct separation of the optically active 3-chloro-1-(substituted) phenyl-1-propanol, formed by the asymmetric hydrolysis, from the optically active 3-chloro-1-(substituted) phenyl-1-propyl ester of a saturated or unsaturated aliphatic acid, which is conducted by, e.g., adding a suitable organic solvent, such as ether and ethyl acetate to the reaction mixture of the enzymatic hydrolysis to extract both of the optically active compounds (the alcohol as a product, and the ester as an unreacted starting material and isolating and purifying the optically active compounds from the extract by silica gel column chromatography, TLC, HPLC, distillation or the like.

Alternatively, a method wherein prior to the respective isolation of the optically active compounds, at least one of the compounds is converted into a derivative is cited.

More particularly, the reaction mixture of the above enzymatic hydrolysis or the extract therefrom containing both of the optically active compounds may be chemically treated to convert at least one of the compounds into a derivative, followed by the respective isolation and purification of the resulting compounds by silica gel column chromatography, TLC, HPLC, distillation or the like.

More particularly, for example, the optically active 3-chloro-1-(substituted) phenyl-1-propanol formed by the hydrolysis is converted into a benzoyl ester by a conventional process using an acid chloride, by which the difference in boiling point between the same and the optically active 3-chloro-1-(substituted) phenyl-1-propyl ester of a saturated or unsaturated aliphatic acid is enlarged, and thereafter both the compounds are separated and purified by distillation.

The optically active 3-chloro-1-(substituted) phenyl-1-propanol or derivative thereof and the optically active 3-chloro-1-(substituted) phenyl-1-propyl ester of a saturated or unsaturated aliphatic acid or derivative thereof separated and purified by the above process can be each used as raw materials for the preparation of various drugs, either as such or after being converted into a suitable derivative as needed. For example, the above ester may be used after being hydrolyzed into an alcohol by a suitable means.

The process of the present invention allows simple and easy preparation of an optically active 3-chloro-1-(substituted) phenyl-1-propanol or a derivative thereof and an optically active 3-chloro-1(substituted) phenyl-1-propyl ester of a saturated or unsaturated aliphatic acid or a derivative thereof, each of which has a high optical purity, thus being extremely industrially advantageous.

The present invention will now be described in more detail by referring to the following Examples, though the present invention is not limited by them.

EXAMPLE 1

213 mg (1 mmol) of racemic 1-acetoxy-3-chloro-1-phenylpropane was put in a 30-ml short-necked flask, followed by the addition of 10 ml of a 0.1M phosphate buffer (pH: 7.2) and 213 mg of "Lipase P, Amano". The obtained mixture was stirred at 36° C. to conduct a reaction. The reaction was monitored by gas chromatography. Four days after the initiation of the reaction, the conversion reached about 50% and the reaction was stopped. The obtained reaction mixture was extracted with 10 ml of ether twice and the ether layers were combined and washed with water. The organic (ether) layer was dried over magnesium sulfate and concentrated under a reduced pressure. The concentrate was chromatographed on a silica gel column [developer: hexane/ethyl acetate=40:1 (v/v)]. 93 mg of (S)-(−)-1-acetoxy-3-chloro-1-phenylpropane was recovered from the first fraction (yield: 43.84%) and 81 mg of (R)-(+)-3-chloro-1-phenyl-propanol from the second fraction (yield: 48.1%).

The configuration was determined by HPLC (developer: n-hexane / isopropanol =19:1 (v/v), 1 ml/min, 40° C. and detection at 254 nm) using a column for optical resolution "Chiral cell OB" (a product of Daicel Chemical Industries, Ltd.).

The physical properties of the obtained optically active compounds are as follows:

(S)-(−)-1-Acetoxy-3-chloro-1 -phenylpropane; $[\alpha]_D^{21}$−58.2 (c=1.34, $CHCl_3$) IR (neat, $cm^{-1}$) 3100, 3050, 2980, 1750, 1610, 1590, 1500, 1460, 1375, 1240, 1030 60 MHz $^1$H-NMR ($CCl_4$, δ) 1.98 (s, 1H, —$COCH_3$), 2.05–2.42 (m, 2H, $CH_2CH_2Cl$), 3.23–3.60 (m, 2H, $CH_2Cl$), 5.80 (dd, J =8 Hz, 5 Hz, 1H, CH), 7.23 (s, 5H)

(R)-(+)-3-Chloro-1-phenylpropanol; $[\alpha]_D^{21}$+29.5 (c=1.12, $CHCl_3$) IR (KBr, $cm^{-1}$) 3300OH), 3050, 2950, 2900, 1500, 1475, 1340, 1300, 1295, 1240, 1200, 1140, 1060, 1040, 1020 60 MHz $^1$H-NMR ($CCl_4$, δ) 1.80–2.35 (m, 2H, $CH_2CH_2l$), 2.10 (br.s, 1H, OH), 3.28–3.92 (m, 2H,—$CH_2Cl$), 4.87 (dd, J=8 Hz, 5 Hz, 1H, CH), 7.31 (s, 5H)

EXAMPLES 2 to 4

The same procedure with respect to the reaction system, reaction and purification as that of Example 1 was repeated except that the enzyme was replaced by one listed in Table 1 and the reaction time was changed to one specified in Table 1. The yield, specific rotation and configuration of each of the obtained optically active compounds were determined in a similar manner to that of Example 1. The results are given in the Table 1.

TABLE 1

| Ex. No. | Enzyme | Reaction time | Obtained alcohol | | | Obtained ester | | |
|---|---|---|---|---|---|---|---|---|
| | | | yield (%) | $[\alpha]_D^{21}$ | configuration | yield (%) | $[\alpha]_D^{21*}$ | configuration |
| 2 | Lipase PS, Amano | 3 day | 47.5 | +26.1 | R | 45.2 | −59.7 | S |
| 3 | Lipase A-6, Amano | 17 hours | 51.0 | −22.9 | S | 44.7 | +52.5 | R |
| 4 | Lipase A-12, Amano | 14 hours | 43.9 | −21.0 | S | 49.4 | +49.4 | R | note)
*: (C = 1, CHCl$_3$)

EXAMPLES 5 to 13

250 mg of racemic 1-acetoxy-3-chloro-1-phenyl-propane was put in a test tube, followed by the addition of 5 ml of a 0.5M phosphate buffer (pH: 7.2) and 250 mg of each of the enzymes listed in Table 2. The resulting mixture was stirred at 26° C. to conduct a reaction. The reaction was monitored by gas chromatography. After the progress of the reaction to a suitable extent has been ascertained, the extraction of the reaction mixture and the purification of the extract were conducted in a similar manner to that of Example 1, and the yield, optical purity and configuration of each of the obtained optically active 1-acetoxy-3-chloro-1-phenylpropane and the obtained optically active 3-chloro-1-phenylpropanol were determined. The results are given in the Table 2.

The optical purity and configuration were determined by HPLC (solvent: n-hexane/isopropanol=19:1 (v/v), 1 ml/min, 40° C. and detection at 254 nm) using a column for optical resolution "Chiral cell OB" (a product of Daicel Chemical Industries, Ltd.).

were obtained and the yield, optical purity and configuration of each of them were determined. The obtained alcohol has the R-configuration and an optical purity of 874 e.e. and its yield was 424, while the obtained ester had the S-configuration and an optical purity of 734 e.e. and its yield was 504.

Example 15

The reaction, extraction and purification were conducted in a similar manner to that of Example 8 except that 250 mg of racemic 1-acetoxy-3-chloro-1-( 4-chlorophenyl)propane was used as the raw material. The yield, optical purity and configuration of each of the obtained optically active compounds were determined. The obtained alcohol had the R-configuration and an optical purity of 824 e.e. and its yield was 32%, while the obtained ester had the S-configuration and an optical purity of 40% e.e. and its yield was 59

We claim:
1. A process for the preparation of an optically active 3-chloro-1-phenyl-1propanol and derivatives thereof, comprising:

(A) treating an enantiometric mixture of a 3-chloro-1-

TABLE 2

| Ex. No. | Enzyme | Reaction time (hr) | Obtained alcohol | | | Obtained ester | | |
|---|---|---|---|---|---|---|---|---|
| | | | yield (%) | configuration | optical purity (% e.e.) | yield (%) | configuration | optical purity (% e.e.) |
| 5 | Lipase MY | 46 | 30 | R | 95 | 60 | S | 50 |
| 6 | Lipase OF | 46 | 48 | R | 96 | 43 | S | 92 |
| 7 | Lipase (Toyo Jozo) | 143 | 20 | R | 88 | 70 | S | 25 |
| 8 | Lipase G | 96 | 15 | R | 90 | 76 | S | 20 |
| 9 | Lipase GC, Amano 20 | 96 | 20 | R | 92 | 71 | S | 30 |
| 10 | Lipase F-AP, Amano 15 | 96 | 12 | S | 80 | 77 | R | 15 |
| 11 | Newlase F, Amano 3 | 96 | 10 | S | 90 | 82 | R | 10 |
| 12 | Palatase A750L | 96 | 20 | S | 90 | 72 | R | 30 |
| 13 | Lipase (Steapsin) | 96 | 10 | R | 70 | 81 | S | 10 |

EXAMPLE 14

250 mg of racemic 1-valeryloxy-3-chloro-1-phenyl-propane was put in a test tube, followed by the addition of 5 ml of a 0.5M phosphate buffer (pH: 7.2) and 250 mg of Lipase OF. The reaction of the resulting mixture and the extraction and purification of the reaction mixture were conducted in a similar manner to that of Example 5 except that the reaction time was changed to 72 hours. Optically active compounds (substituted) phenyl-1-propyl ester of a saturated or unsaturated aliphatic acid represented by the formula (1):

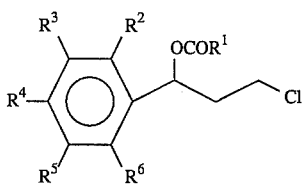

(1)

wherein $R^1$ is a saturated or unsaturated, straight chain or branched, monovalent hydrocarbon group having 1 to 18 carbon atoms; or a saturated or unsaturated straight chain or branched, monovalent halogenohydrocarbon group having 1 to 18 carbon atoms; and $R^2$, $R^3$, $R^4$, $R^5$, $R^6$ are independently selected from the group consisting of a hydrogen atom, a halogen atom, a nitro group, a hydroxyl group, a straight chain or branched alkyl group having 1 to 6 carbon atoms and an alkoxy group, wherein said alkoxy group has an alkyl moiety which is straight chain or branched, and has 1 to 4 carbon atoms; with an lipase which can asymmetrically hydrolyze said enantiomeric mixture to form a product mixture comprising optically active 3-chloro-1-(substituted) phenyl-1-propanol and an optically active 3-chloro-1-(substituted) phenyl-1-propyl ester of a saturated or unsaturated aliphatic acid, wherein said lipase is obtained from a microoganism selected from the group consisting of *Aspergillus niger Candida cylindracea Chromobacterium viscosum, Penicillium cyclopium Geotrichum candidum, Rhizopus japonicus,* and *Rhizopus niveus*; and (B) recovering said optically active 3-chloro-1-phenyl-1-propanol and derivatives thereof.

2. The process for the preparation of an optically active 3-chloro-1-phenyl-1-propanol and derivatives thereof as set forth in claim 1, wherein said optically active 3-chloro-1-(substituted) phenyl-1-propanol and said optically active 3-chloro-1-(substituted) phenyl-1-propyl ester of a saturated or unsaturated aliphatic acid are separately recovered from said product mixture.

3. The process for the preparation of an optically active 3-chloro-1-phenyl-1-propanol and derivatives thereof as set forth in claim 1, further comprising chemically treating said product mixture to convert at least one of said optically active 3-chloro-1-(substituted)phenyl-1-propanol and said optically active 3-chloro-1-(substituted) phenyl-1-propyl ester of a saturated or unsaturated aliphatic acid into a derivative and separately recovering said optically active 3-chloro-1-(substituted) phenyl-1-propanol or its derivative, and the optically active 3-chloro-1-(substituted) phenyl-1-propyl ester of a saturated or unsaturated aliphatic acid or its derivative.

4. The process according to claim 3, wherein said chemical treatment comprises chemically converting said optically active 3-chloro-1-(substituted) phenyl-1-propanol to an ester.

5. The process according to claim 4, wherein said chemical treatment comprises chemically converting said optically active 3-chloro-1-(substituted) phenyl-1-propanol to a benzoyl ester.

6. The process for the preparation of an optically active 3-chloro-1-phenyl-1-propanol and derivatives thereof as set forth in claim 1, wherein $R^1$ is an aliphatic hydrocarbon group having 1 to 8 carbon atoms; and $R^2$, $R^3$, $R^4$, $R^5$, and $R^6$ are each a hydrogen atom.

7. The process for the preparation of an optically active 3-chloro-1-phenyl-1-propanol and derivatives thereof as set forth in claim 1, wherein said optically active 3-chloro-1-(substituted) phenyl-1-propanol has the R-configuration and said optically active 3-chloro-1-(substituted) phenyl-1-propyl ester of a saturated or unsaturated aliphatic acid has the S-configuration.

8. The process for the preparation of an optically active 3-chloro-1-phenyl-1-propanol and derivatives thereof as set forth in claim 1, wherein said optically active 3-chloro-1-(substituted) phenyl-1-propanol has the S-configuration and said optically active 3-chloro-1-(substituted) phenyl-1-propyl ester of a saturated or unsaturated aliphatic acid has the R-configuration.

9. A process for the preparation of an optically active 3-chloro-1-phenyl-1-propanol and derivatives thereof, comprising:

(A) treating an enantiomeric mixture of a 3-chloro-1-(substituted) phenyl-1-propyl ester of a saturated or unsaturated aliphatic acid represented by the formula (1):

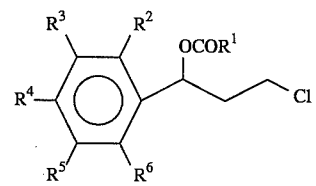

(1)

wherein $R^1$ is a saturated or unsaturated, straight chain or branched, monovalent hydrocarbon group having 1 to 18 carbon atoms, or a saturated or unsaturated straight chain or branched, monovalent halogenohydrocarbon group having 1 to 18 carbon atoms; and $R^2$, $R^3$, $R^4$, $R^5$, $R^6$ are independently selected from the group consisting of a hydrogen atom, a halogen atom, a nitro group, a hydroxyl group, a straight chain or branched alkyl group having 1 to 6 carbon atoms and an alkoxy group, wherein said alkoxy group has an alkyl moiety which is straight chain or branched, and has 1 to 4 carbon atoms; with an enzyme capable of asymmetrically hydrolyzing said enantiomeric mixture to form a product mixture comprising optically active 3-chloro-1-(substituted) phenyl-1-propanol and an optically active 3-chloro-1-(substituted) phenyl-1-propyl ester of a saturated or unsaturated aliphatic acid, wherein said enzyme is at least one lipase selected from the group consisting of Lipase A-6, Lipase A-12, Lipase MY, Lipase OF, Lipase (Toyo Jozo), Lipase G, Lipase GC, Lipase F-AP, Newlase F, and Palatase A750L; and (B) recovering said optically active 3-chloro-1-phenyl-1-propanol and derivatives thereof.

10. A process for the preparation of an optically active 3-chloro-1-phenyl-1-propanol and derivatives thereof, comprising:

(A) treating an enantiomeric mixture of a 3-chloro-1-(substituted) phenyl-1propyl ester of a saturated or unsaturated aliphatic acid represented by the formula (1):

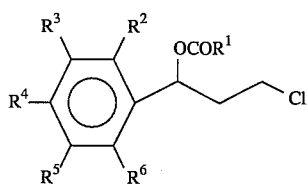

(1)

wherein $R^1$ is a saturated or unsaturated, straight chain or branched, monovalent hydrocarbon group having 1 to 18 carbon atoms, or a saturated or unsaturated straight chain or branched, monovalent halogenohydrocarbon group having 1 to 18 carbon atoms; and $R^2$, $R^3$, $R^4$, $R^5$, $R^6$ are independently selected from the group consisting of a hydrogen atom, a halogen atom, a nitro group, a hydroxyl group, a straight chain or branched alkyl group having 1 to 6 carbon atoms and an alkoxy group, wherein said alkoxy group has an alkyl moiety which is straight chain or branched, and has 1 to 4 carbon atoms; with an enzyme capable of asymmetrically hydrolyzing said enantiomeric mixture to form a product mixture comprising optically active 3-chloro-1-(substituted) phenyl-1-propanol and an optically active 3-chloro-1-(substituted) phenyl-1-propyl ester of a saturated or unsaturated aliphatic acid, wherein said enzyme is at least one lipase selected from the group consisting of Lipase F-AP, Newlase F, and Palatase ; and (B) recovering said optically active 3-chloro-1-phenyl-1-propanol and derivatives thereof.

* * * * *